(12) United States Patent
Serra et al.

(10) Patent No.: US 7,255,702 B2
(45) Date of Patent: Aug. 14, 2007

(54) BONE MILLING INSTRUMENT

(76) Inventors: Michael A. Serra, 4607 Hillwood Dr., Shingle Springs, CA (US) 95682; Shaun B. Hanson, 137 E. Phoenix Dr., Phoenixville, PA (US) 19460; Alfred S. Despres, III, 4607 Hillwood Dr., Shingle Springs, CA (US) 95862

( * ) Notice: Subject to any disclaimer, the term of this patent is extended or adjusted under 35 U.S.C. 154(b) by 399 days.

(21) Appl. No.: 10/435,574

(22) Filed: May 9, 2003

(65) Prior Publication Data

US 2004/0092951 A1    May 13, 2004

Related U.S. Application Data

(60) Provisional application No. 60/378,985, filed on May 9, 2002.

(51) Int. Cl.
*A61B 17/00* (2006.01)
(52) U.S. Cl. ...................................................... 606/80
(58) Field of Classification Search .................. 606/80, 606/79, 84, 87, 86, 96, 97–98, 99, 54–56, 606/57–59
See application file for complete search history.

(56) References Cited

U.S. PATENT DOCUMENTS

| | | | |
|---|---|---|---|
| 4,777,942 A * | 10/1988 | Frey et al. ..................... 606/80 |
| 5,342,366 A | 8/1994 | Whiteside et al. |
| 5,468,243 A | 11/1995 | Halpern |
| 5,496,324 A * | 3/1996 | Barnes ........................ 606/79 |
| 5,527,316 A * | 6/1996 | Stone et al. .................. 606/80 |
| 5,540,694 A | 7/1996 | DeCarlo, Jr. et al. |
| 5,645,548 A * | 7/1997 | Augsburger ................. 606/87 |

\* cited by examiner

*Primary Examiner*—Alvin J. Stewart
(74) *Attorney, Agent, or Firm*—Pandiscio & Pandiscio

(57) ABSTRACT

A bone milling instrument is disclosed for creating a shaped cavity from an initial cavity in a bone, the bone milling instrument comprising a reference frame, a centering member at the distal end of the reference frame, a registration surface for engaging a portion of the initial cavity, and an attachment site provided proximally of the registration surface, a guidance support member, an attachment mechanism at the first end of the guidance support member, and a constrained pathway extending between the ends of the guidance support member; a shuttle having a first connection element configured for positionably attaching the shuttle to the guidance support member, and a second connection element configured to provide a rotational coupler; and a cutting device having a cutting portion configured at a distal end thereof, and an attachment portion provided at a proximal end.

15 Claims, 9 Drawing Sheets

BONE MILLING INSTRUMENT

REFERENCE TO PENDING PRIOR PATENT APPLICATION

This patent application claims benefit of now abandoned prior U.S. Provisional Patent Application Ser. No. 60/378,985, filed May 9, 2002 by Shaun B. Hanson et al. for BONE MILLING INSTRUMENT, which patent application is hereby incorporated herein by reference.

FIELD OF THE INVENTION

This invention is related to orthopedic implant apparatus and methods in general, and more particularly to apparatus and methods for creating a shaped cavity in a bone.

SUMMARY OF THE INVENTION

This invention provides a bone milling instrument designed to create a cavity in bone for orthopedic implants. The instrument removes a volume of bone using a rotating cutter which progresses along a set path. The shape of the volume of bone is determined by the direction of the set path, the location of the path relative to the bone, and the shape of the cutter and/or cutters used. By engineering the combination of translations and rotations of the cutting tool in space, as controlled by the path, anatomically accurate geometries may be machined into the bone. Of particular interest is the milling of the medial arc portion of the proximal femur which is typically defined as an arc or compound curve having tapered sides. The instrument consists of a system of components including a stationary reference frame, a guidance support member, a reamer shuttle, and a cutting device. The guidance support member can be adjusted vertically and horizontally to change the size, shape, and location of the cavity created.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BACKGROUND OF THE INVENTION

In orthopedic total joint replacement surgery it is necessary for the implant to be securely fixed to the host bone for a successful clinical outcome. Normally this is accomplished in one of two ways; either the implant is fixed to the bone using a surgical cement, or it is forcefully pressed into the bone to achieve an interference fit. When the implant is to be press-fit into the bone, a cavity is created in the bone to receive the geometry of the implant. For the press-fit method, it is important that this cavity closely fits the implant shape in order to hold the implant securely in the bone.

Currently, there are two common methods for creating this cavity in the bone for the implant. One method used is to remove bone material using a set of rasps or broaches and a mallet. The other method is to remove bone by milling the bone with a set of reamers, drills, or other revolving cutting tools. The method of this invention is that of milling the bone with cutting instruments. Examples of devices that use milling instruments to machine the bone include those found in U.S. Pat. Nos. 5,540,694 (De Carlo, Jr. et al.), U.S. Pat. No. 5,342,366 (Whiteside et al.), and U.S. Pat. No. 4,777,942 (Frey et al.).

Current milling instrumentation systems are unable to machine shapes that match the naturally occurring internal anatomy of the bone. Due to the nature of using revolving cutting tools, the implant designs driven by these instrumentation systems consist of rudimentary combinations of cones and cylinders. Preparing bone for implants of these basic shapes often causes one to compromise the fit of the implant to the bone. The implant cavity prepared with milling is very simple and the anatomy of the bone is much more complex. Implanting non-anatomic geometries requires removing more bone in some areas and less bone in other areas than is desirable. Using the broach/rasp system, more complex and anatomically correct implant shapes can be created in the bone, when compared to those geometries which can be milled into the bone using simple cone and cylinder instrumentation. Although broach/rasp systems can create a more anatomically correct shape in the bone, the act of repeatedly hammering the broach/rasp in and out of the bony canal is imprecise. On the other hand, previous milling systems were able to create accurate holes in the bone which were too simple to be anatomically correct. Anatomically correct implants typically include arcs or compound arcs having parallel or tapered sides. These arcs can be either symmetrically or asymmetrically placed relative to the bulk of the proximal implant geometry.

SUMMARY OF THE INVENTION

The purpose of this invention is to allow the surgeon to create shaped cavities within bones. These cavities have complex and compound arcs of various geometries and are created using rotating cutting tools. The milling instrument can remove a volume of bone while progressing along a path of simple or complex arcs (rotations), single or multiple lines (translations), or a combination of both translations and rotations. These cavities can be created either symmetric or asymmetric relative to any given axis of the bone. This milling instrumentation can be adjusted vertically and horizontally to change the size, shape, and location of the milled cavity to match the anatomic shape of the bone in the region.

The milling instrument described in this invention is a system of four components: a reference frame, a guidance support member, a reamer shuttle, and a cutting device. The reference frame acts as a support and positional reference for the cutting tool with respect to the bone. The guidance support member controls the path of the cutting tool and thus governs the resulting cavity shape constructed in the bone. The guidance support member can be adjusted in different directions and orientations with respect to the reference frame to alter the shape, size, and location of the cavity created in the bone. The cutting device can be simply a tapered reamer or a revolving cutter of any shape designed to remove material by revolving about its central axis. The reamer shuttle is a component that allows the cutting device to rotate freely while constraining its motion to follow the guidance track. This invention can be a system of components where each of the components is separable and interchangeable with another one of a different size and/or configuration.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

Figure 1:
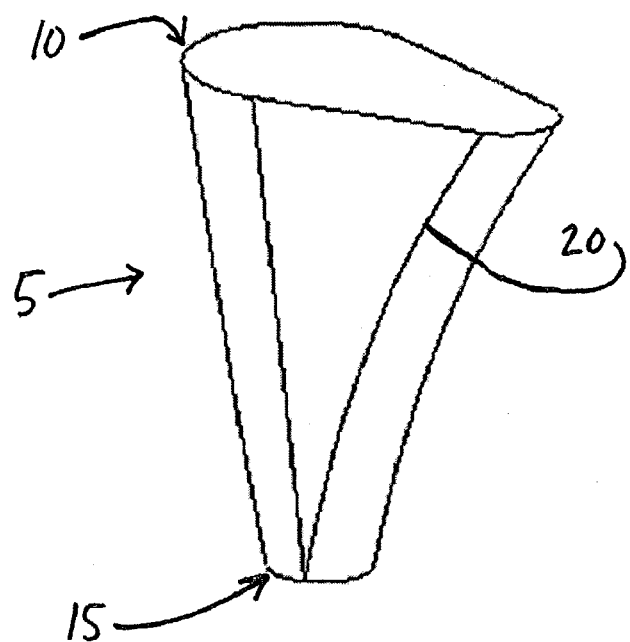
FIGS. 1 and 2 are schematic illustrations of a shaped cavity illustrated as a solid object without the surrounding bone.
Figure 2:
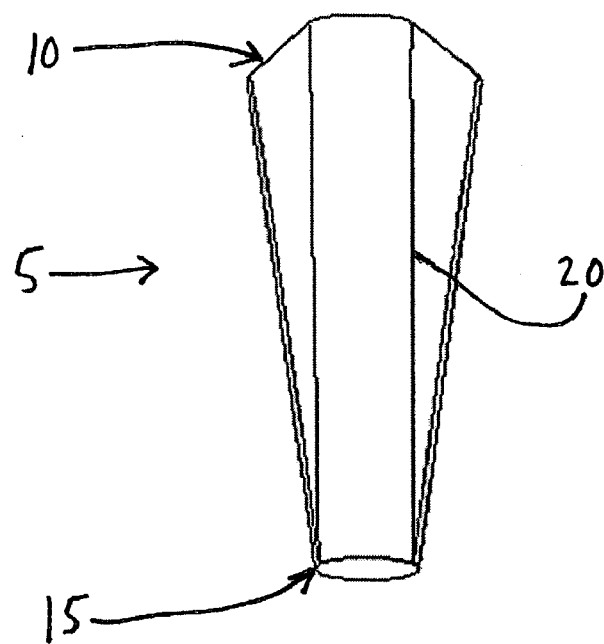

Referring to FIGS. 1 and 2, and in a preferred embodiment of the present invention, there is shown a first shaped cavity 5, which is illustrated as a solid object 5 but is actually a void within bone (not shown). Such a cavity 5 is preferably wedge shaped and has two ends, including a large end 10 and a smaller end 15, with tapering sides 20 that form at a compound angle to the central axis of the cavity.

Figure 3:
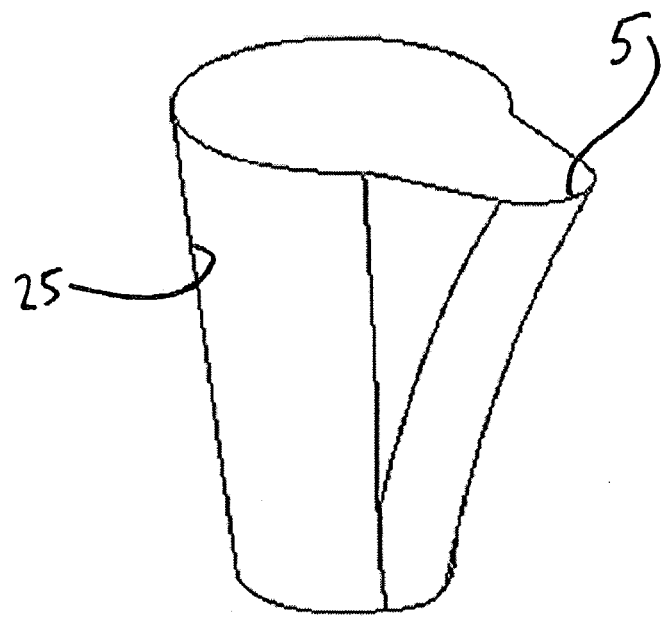
FIG. 3 is a schematic illustration of a composite cavity formed by the intersection of a tapered cavity and a conical cavity with one another.
Figure 4:
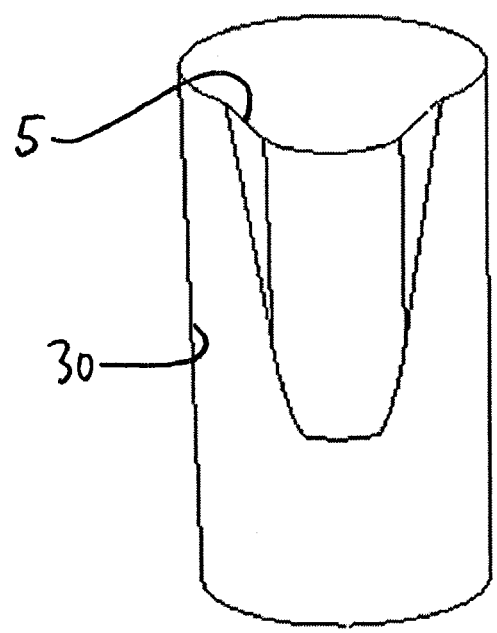
FIG. 4 is a schematic illustration of a composite cavity formed by the intersection of a tapered cavity and a cylindrical cavity with one another.

As shown in FIGS. 3 and 4, tapering cavity 5 can be intersected with other shaped cavities including, but not limited to, a cone 25 (FIG. 3) or a cylinder 30 (FIG. 4), so as to form a composite shape that would conform to the implant.

Figure 5:
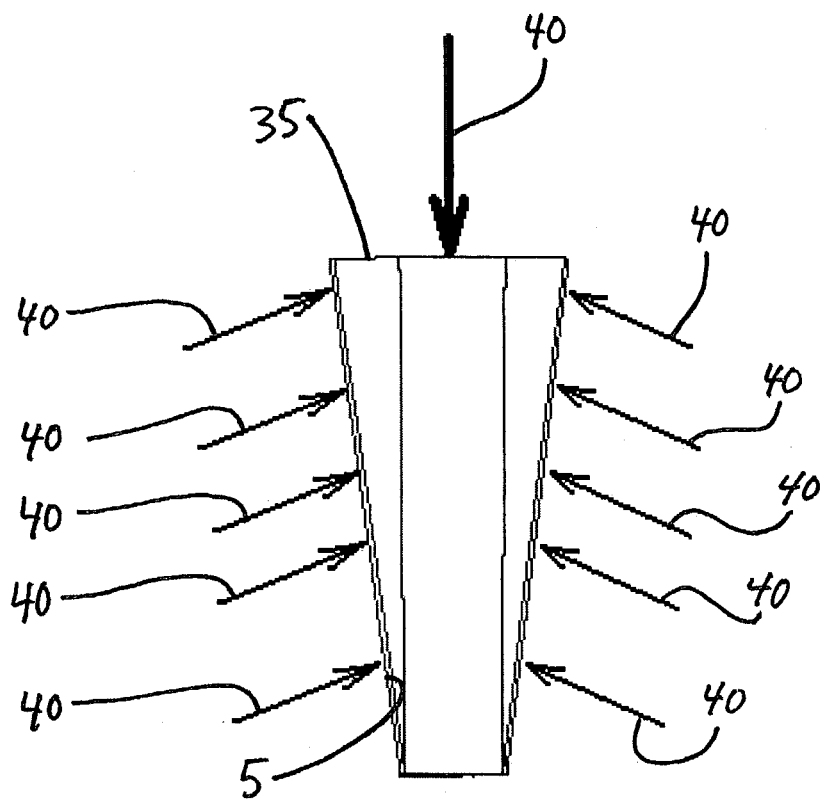
FIG. 5 is a schematic illustration of an implant disposed within a shaped cavity and force arrows representing transfer loads applied evenly to the bone.

Referring now to FIG. 5, there is shown an implant 35 disposed within cavity 5. Cavity 5 has tapering sides designed to transfer loads evenly to the bone as indicated by arrows 40. This configuration will also stimulate bone growth.

Figure 6:
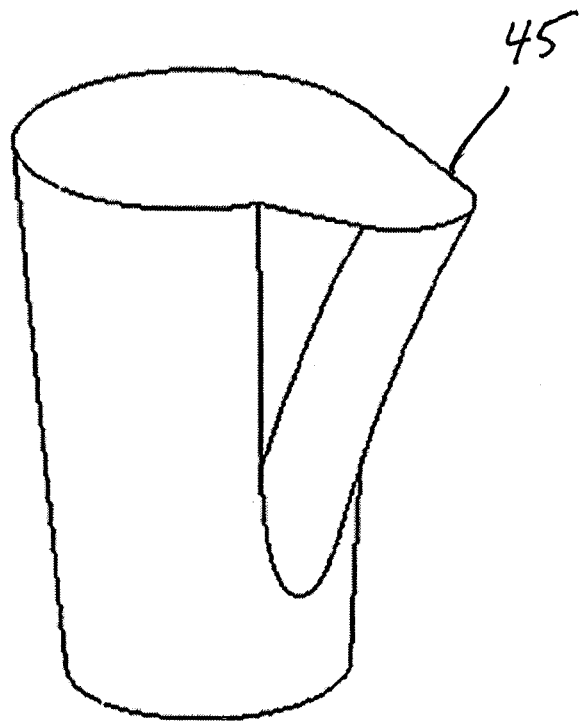
FIGS. 6 and 7 are schematic illustrations of a composite cavity including a non-symmetric tapered portion.
Figure 7:
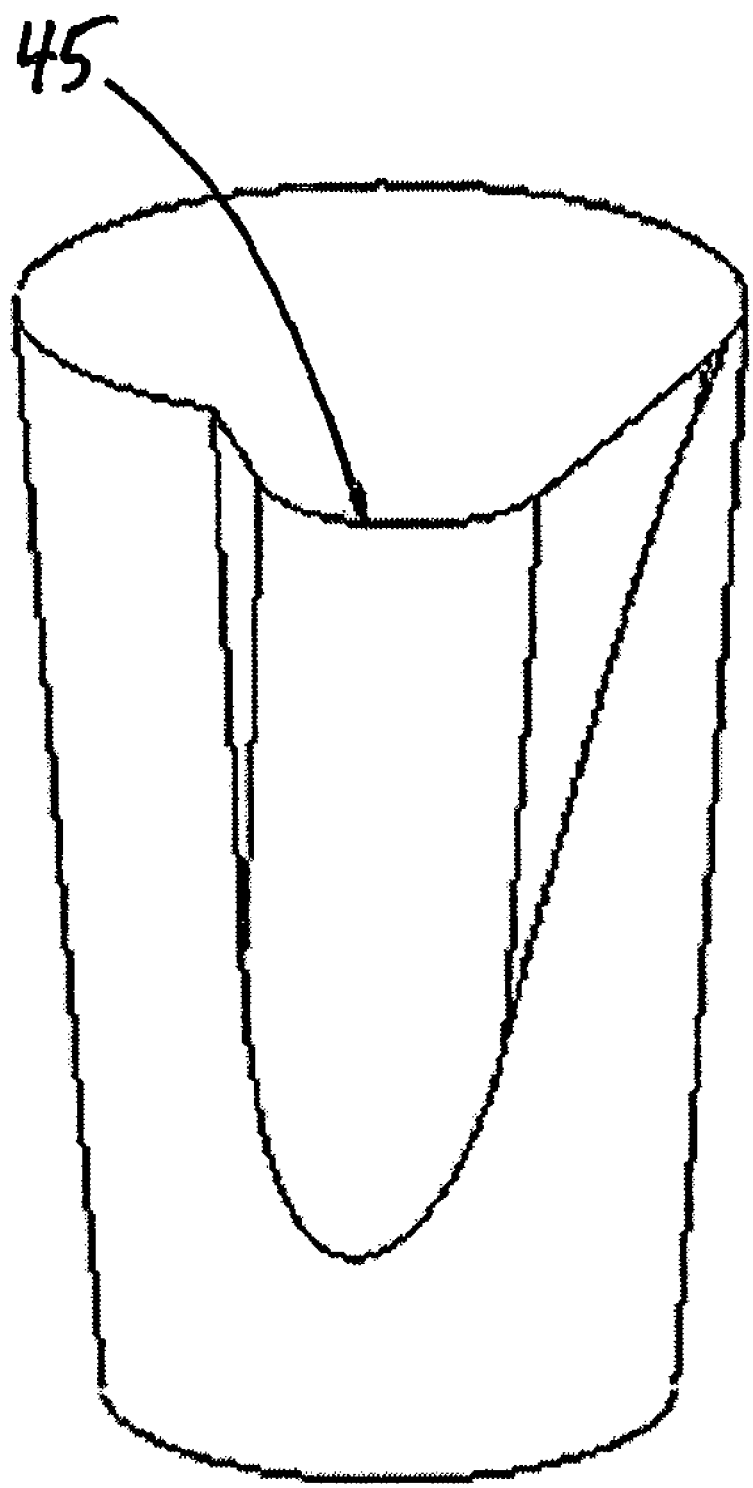

The instrument can create the wedge opening along a curve (such as a medial curve) or along another specified path. The instrument can also create the larger opening of the cavity off-axis to the longitudinal axis of the bone, thus creating a non-symmetric, and perhaps more anatomically fitting, cavity 45 within the bone as shown in FIGS. 6 and 7.

Figure 8:
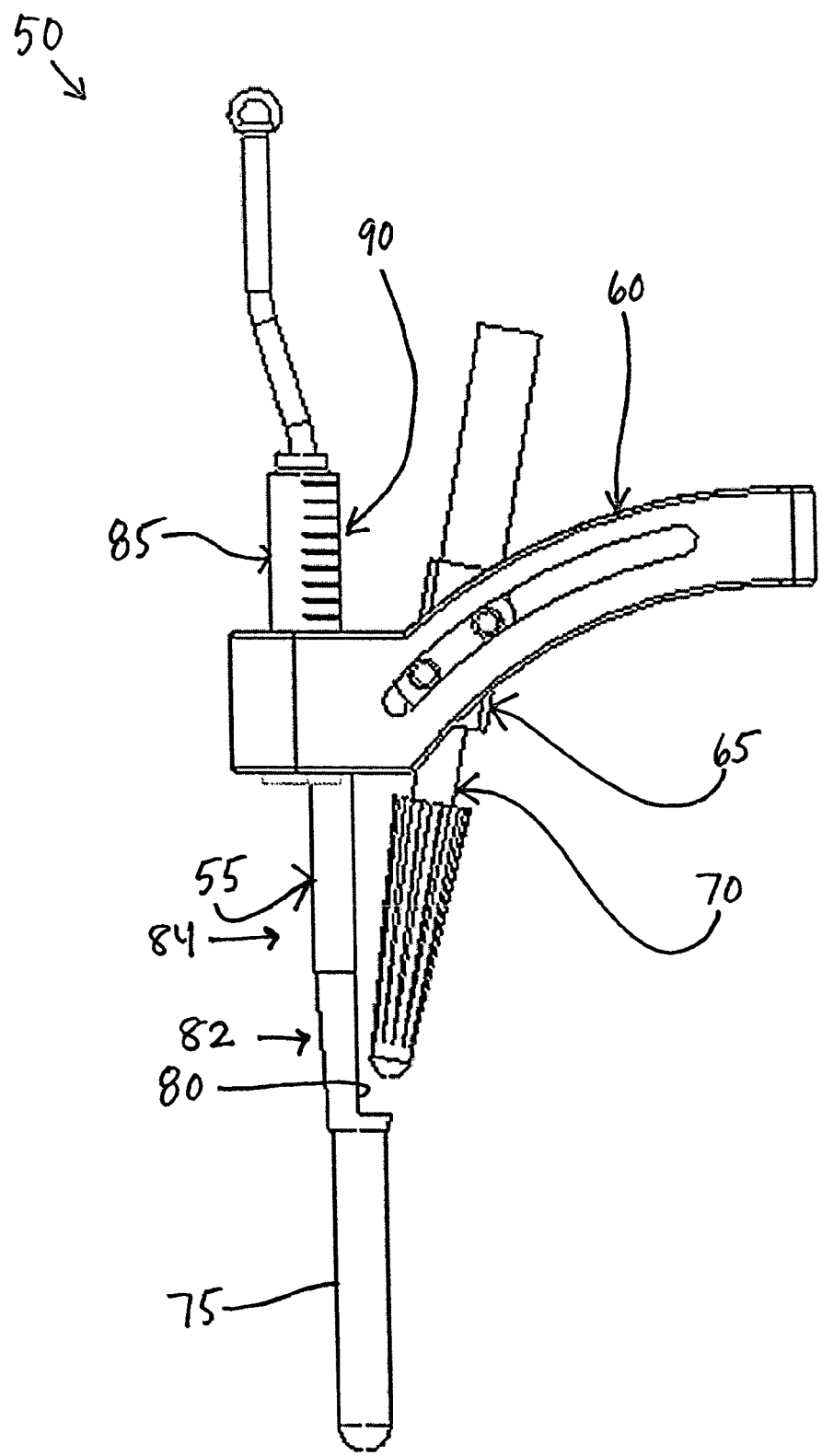
FIG. 8 is a schematic illustration of a preferred embodiment of a bone milling instrument.

Looking now at FIG. 8, an in a preferred embodiment of the present invention, there is shown a milling instrument system 50 comprising four components or sub-systems to create a shaped cavity. These components include a reference frame 55, a guidance support member 60, a reamer shuttle 65, and a cutting device 70. The components of the system shown can vary and be interchangeable with other components.

Figure 9:
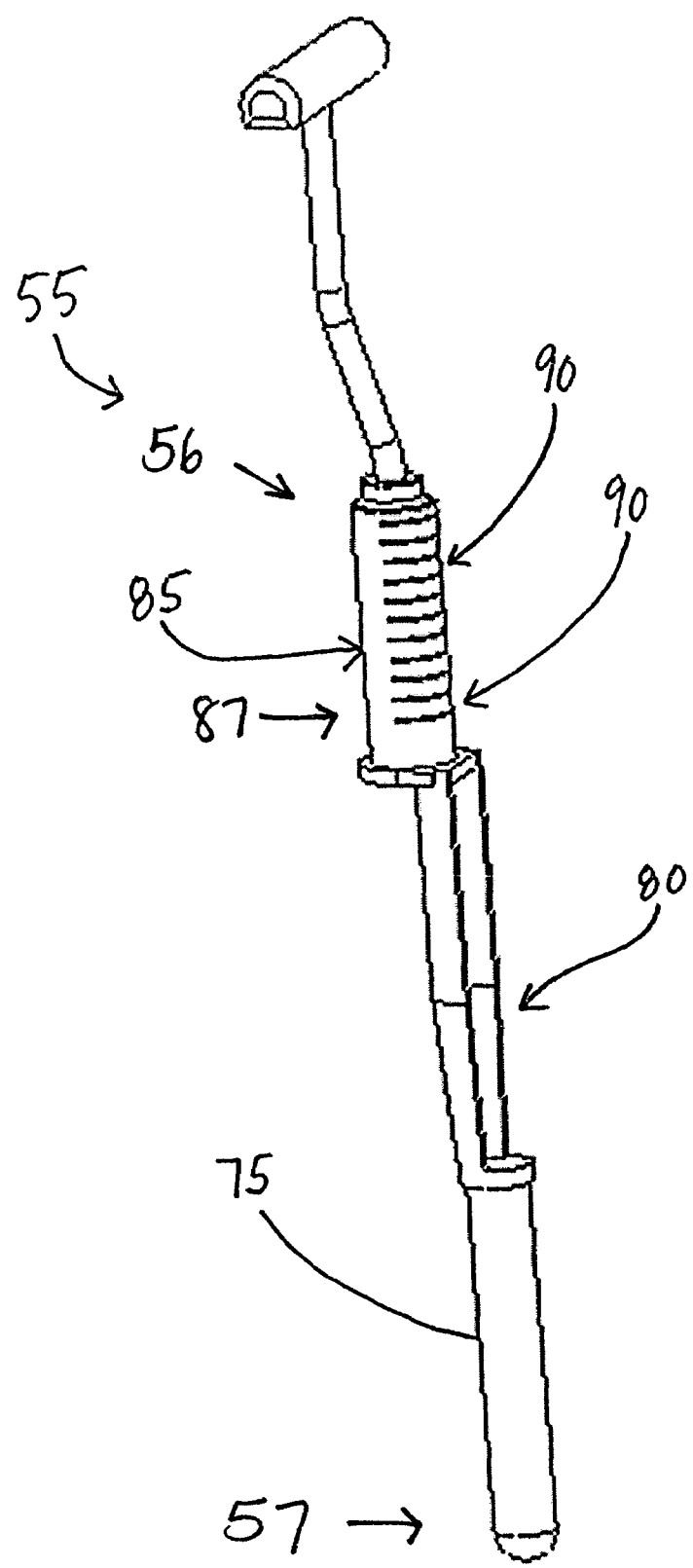
FIG. 9 is a schematic illustration of a reference frame component of the bone milling instrument.

Referring now to FIG. 9, there is shown another view of reference frame 55. During use, reference frame 55 is fixed to and aligned with the longitudinal axis of the bone so as to rest within a cavity that is created prior to inserting the remaining components of milling instrument system 50. Frame 55 provides a reference so that the cavity to be created is positioned at the desired location with respect to the previously formed cavity or opening. Reference frame 55 comprises proximal end 56 and distal end 57. Integral to frame 55 is an axial, cylindrical member 75 that centers the frame on the distally reamed opening in the bone. This is connected to a registration surface 80 that fits the previously formed opening (such as a conical cavity) such that the vertical position of frame 55 to this opening is established. In one embodiment, registration surface 80 has a conical shape 82 and a cylindrical shape 84 (FIG. 8). From registration surface 80 along the central axis protrudes a member 85 for connection of reference frame 55 to the guidance support member 60. More particularly, guidance support member 60 may be attached to member 85 at attachment site 87. Member 85 has vertical markings 90 and/or other features to allow one to adjust position of the guidance support member 60 with respect to reference frame 55, and thus ultimately with respect to the initial opening.

Figure 10:
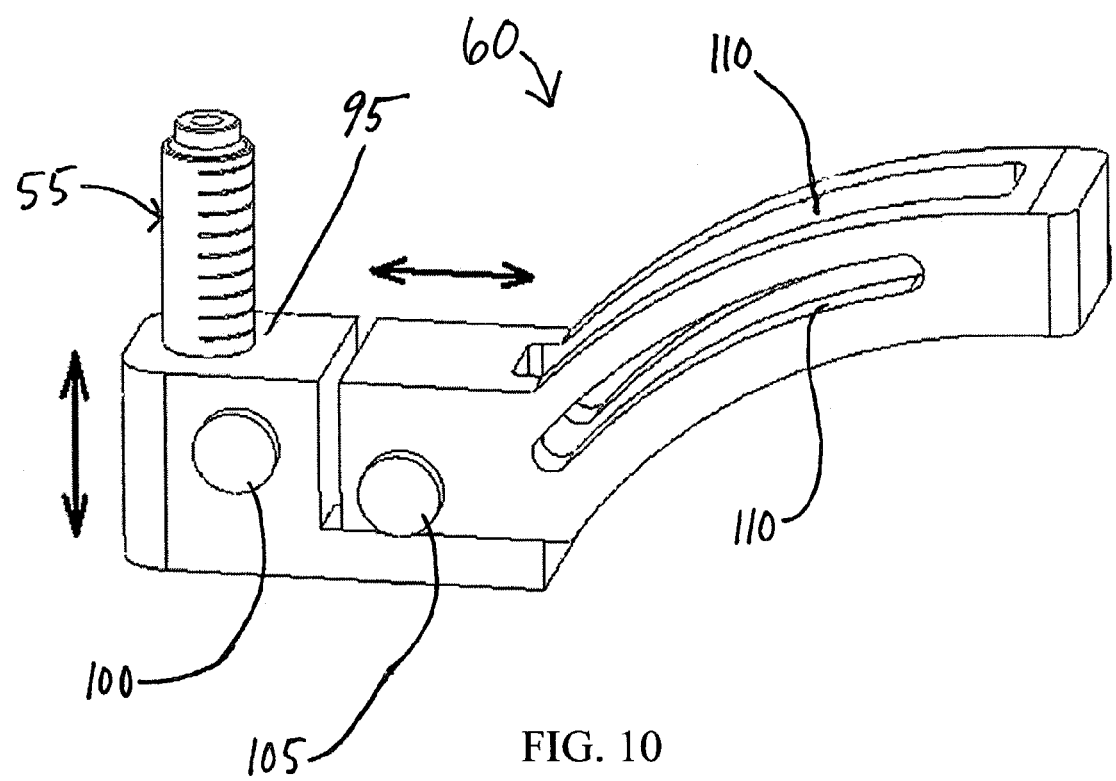
FIG. 10 is a schematic illustration of a guidance support member of the bone milling instrument.

Looking now at FIG. 10, there is shown another view of guidance support member 60 comprising an attachment mechanism 95 for adjustable connection to member 85. Attachment mechanism 95 comprises a vertical adjustment 100 and a horizontal adjustment 105 so as to allow guidance support member 60 to be adjusted vertically and horizontally along frame 55 with respect to the location of the bone. Guidance support member 60 provides a constrained path 110, within which reamer shuttle 65 can travel.

In another preferred embodiment of the present invention (not shown), a guidance support member may provide alternative types of tracks that are interchangeably connected to attachment mechanism 95 that vertically and horizontally positions the track with respect to frame 55. It is also possible that this attachment mechanism 90 can be configured so that constrained area 110 is placed offset and at an angle to the central axis of the reference frame 55. Thus, the key benefit of adjusting guidance support member 60 in any position or orientation allows the creation of a variety of differently located, sized, and shaped cavities. In another preferred embodiment of the present invention (not shown), constrained area 110 comprises multiple guidance rails or individual paths therein.

Figure 11:
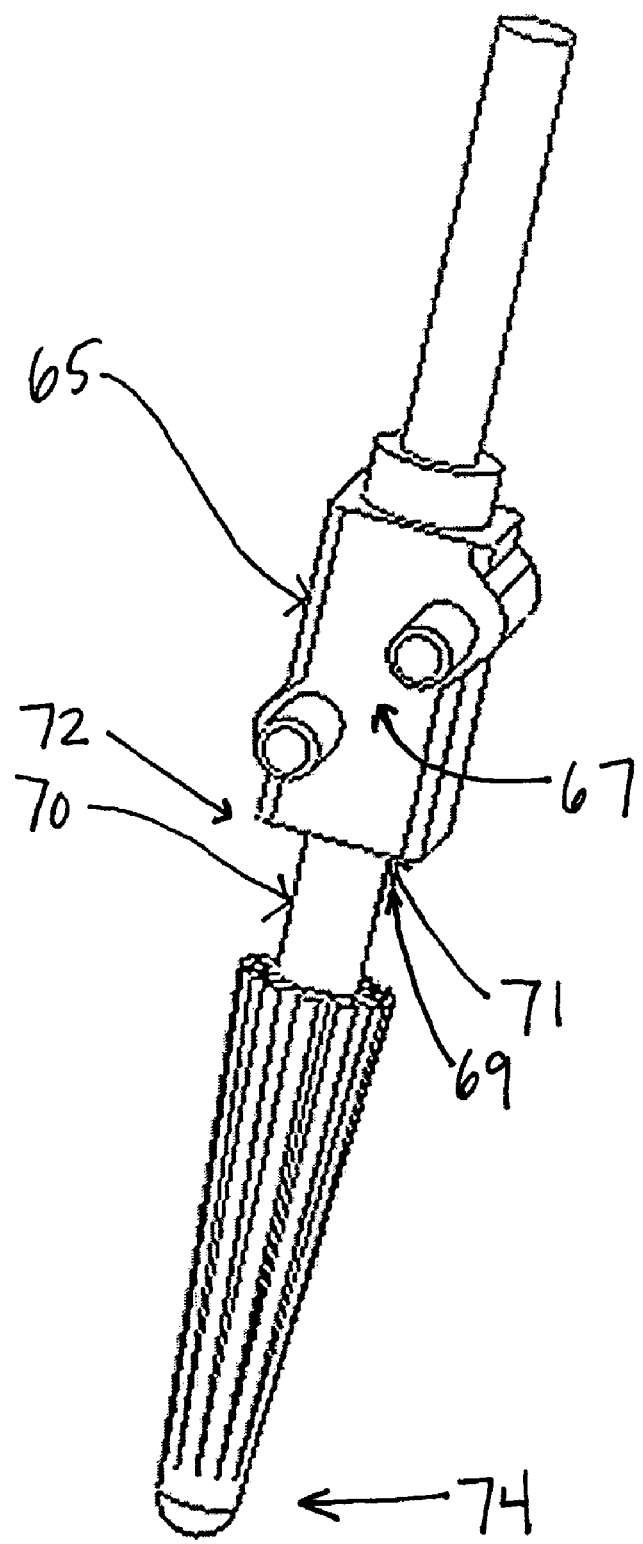
FIG. 11 is a schematic illustration of a shuttle and a cutting device of the bone milling instrument.
Figure 12:
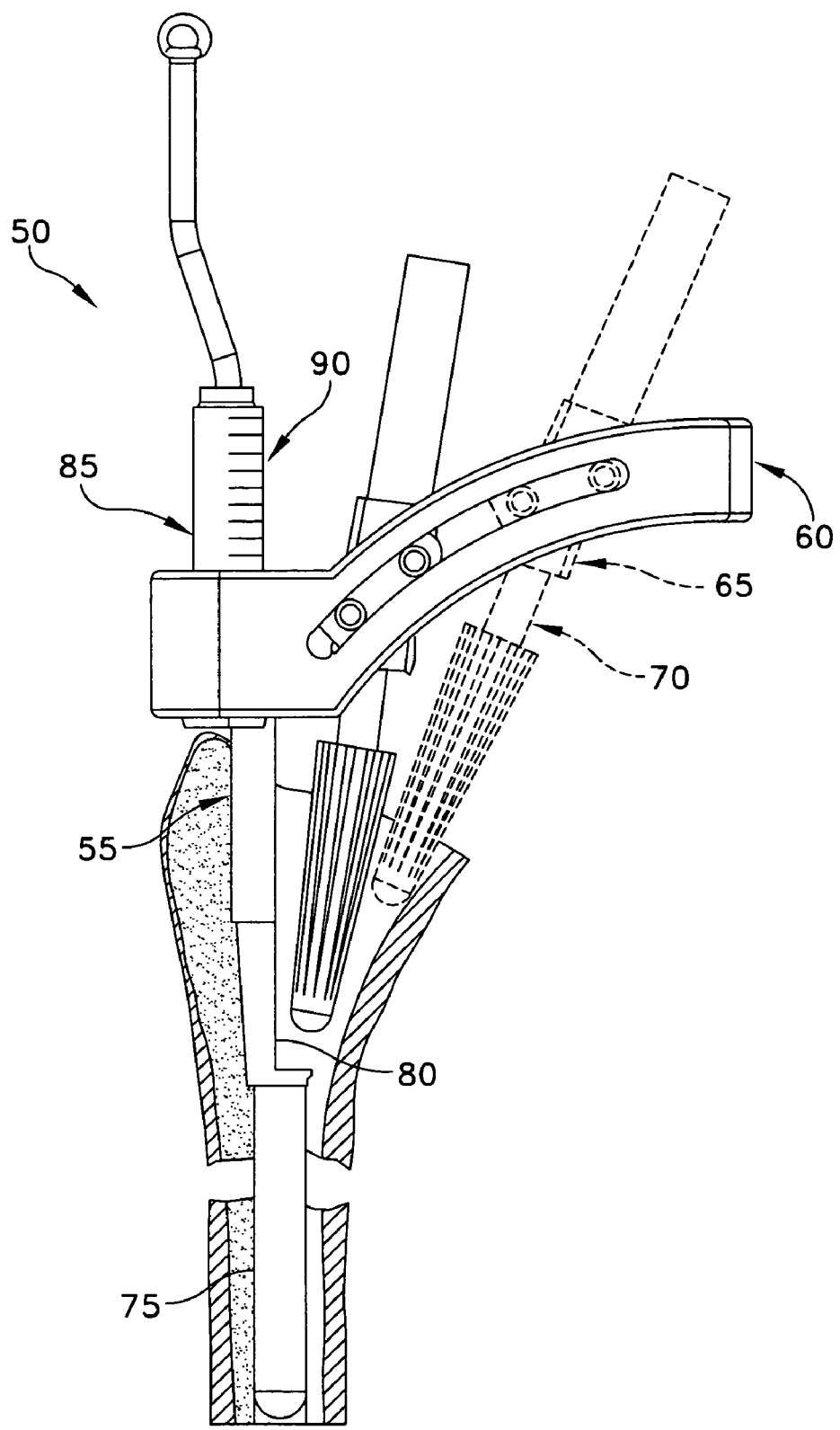
FIG. 12 is a schematic illustration of a method of creating a cavity using the bone milling instrument.

Referring now to FIG. 11, there is shown another view of reamer shuttle 65 comprising cutting device 70 rotatably held therein. Reamer shuttle 65 comprises a first connection element 67 and a second connection element 69. First connection element 67 is configured for positionably attaching reamer shuttle 65 to guidance support member 60 so as to allow movement of reamer shuttle 65 within constrained path 110. Second connection element 69 is configured to provide a rotational coupler 71 within reamer shuttle 65.

Cutting device 70, having a proximal end 72 and a distal end 74, which includes, for example, a revolving mill or cutter configured at distal end 74 and an attachment portion provided at proximal end 72. Cutting device 70 is selectively attached to rotational coupler 71 within reamer shuttle 65 so cutting device 70 is allowed to revolve freely within reamer shuttle 65 while constrained within a path set by guidance support member 60. As the cutting device 70 rotates and follows the path provided by guidance support member 60, the cavity is created in the bone. Although the cutting path as shown in FIGS. 8 and 10 lies in a single plane, different components for constrained path 110 can be placed in guidance support member 60 so as to create complex and compound pathways comprised of multiple translations and rotations about multiple axes. Working in two planes only, off-axis or asymmetric cavities can be machined relative to the bone. The reamer shuttle is designed such that it would operate in interchangeable tracks. Cutting device 70 can be side cutting, end cutting, or both and is designed to cut while rotating. Cutting device 70 and reamer shuttle 65 are constructed such that cutting device 70 is constrained within reamer shuttle 65 so that the only relative motion between each component is the cutting device 70 rotating freely inside reamer shuttle 65.

This disclosed method differs from existing devices that machine bone in that a cutting device is permitted to travel through a path requiring translation and rotation of the cutting tool over at least a portion of said path. In addition, path of the cutting tool is not confined to a single plane or angle.

What is claimed is:

1. A bone milling instrument for creating a shaped cavity from an initial cavity in a bone, the bone milling instrument comprising:
   a reference frame comprising a proximal end and a distal end, the reference frame defining a longitudinal axis between the proximal end and the distal end, a cylindrical member provided at the distal end of the reference frame, the cylindrical member configured for placement within the initial cavity so as to selectively maintain a relative positioning of the longitudinal axis of the reference frame and the bone with one another, a registration surface for engaging a portion of the initial cavity so as to establish a desired vertical position of the reference frame along the longitudinal axis, the registration surface being located proximally of the cylindrical member, and an attachment site provided proximally of the registration surface;
   a guidance support member comprising a first end and a second end, an attachment mechanism at the first end of the guidance support member for adjustable connection thereof at the attachment site of the reference frame, and an arc-shaped constrained pathway extending between the first end and the second end of the guidance support member;
   a shuttle comprising a first connection element and a second connection element, the first connection element configured for positionably attaching the shuttle to the guidance support member so as to contain movement of the shuttle along the constrained pathway; and the second connection element connected to a rotational coupler within the shuttle; and
   a cutting device comprising a proximal end and a distal end, a cutting portion configured at the distal end of the cutting device, and an attachment portion provided at the proximal end, wherein the cutting device is attached to the rotational coupler only within the shuttle at the attachment portion, with the distal end of the cutting device being free-standing relative to the reference frame, so as to allow rotational motion of the cutting portion as the shuttle is moved along the arc-shaped constrained pathway, thereby creating a shaped cavity from the initial cavity in the bone.

2. A bone milling instrument according to claim 1 wherein the reference frame comprises a registration surface which is conical in shape.

3. A bone milling instrument according to claim 1 wherein the reference frame comprises a registration surface which is cylindrical in shape.

4. A bone milling instrument according to claim 1 wherein the cylindrical member of the reference frame is modular.

5. A bone milling instrument according to claim 1 wherein the guidance support member comprises one track.

6. A bone milling instrument according to claim 1 wherein the guidance support member further comprises multiple tracks.

7. A bone milling instrument according to claim 1 wherein the guidance support member further comprises selectively repositionable attachment means for selective positioning of the guidance support member relative to the reference frame, wherein the guidance support member can be placed in a series of fixed positions relative to the reference frame so as to define a range of discrete sized cavities within the bone.

8. A bone milling instrument according to claim 1 wherein the guidance support member is positioned asymmetrically to the longitudinal axis of the reference frame.

9. A bone milling instrument according to claim 1 wherein the cutting device comprises a conical cutting surface so as to produce a cavity having a biplanar wedge shape.

10. A bone milling instrument according to claim 1 wherein the cutting device comprises a cylindrical cutting surface so as to produce a cavity having parallel sides.

11. A bone milling instrument according to claim 1 wherein the cutting device comprises a curved tapering cutting surface so as to produce a cavity that has curved tapering walls.

12. A bone milling instrument according to claim 1 wherein the reference frame is rotationally positionable about the longitudinal axis thereof so as to establish the orientation of the shaped cavity in the bone.

13. A bone milling instrument according to claim 1 wherein the cutting device is translationally and rotationally movable so as to produce a substantially variable angle of the cutting device relative to the longitudinal axis of the reference frame.

14. A method for creating a shaped cavity from an initial cavity in a bone, the method comprising:
   providing a bone milling instrument for creating a shaped cavity from an initial cavity in a bone, the bone milling instrument comprising:
      a reference frame comprising a proximal end and a distal end, the reference frame defining a longitudinal axis between the proximal end and the distal end, a cylindrical member provided at the distal end of the reference frame, the cylindrical member configured for placement within the initial cavity so as to selectively maintain a relative positioning of the longitudinal axis of the reference frame and the bone with one another, a registration surface for engaging a portion of the initial cavity so as to establish a desired vertical position of the reference frame along the longitudinal axis, the registration surface being located proximally of the cylindrical member, and an attachment site provided proximally of the registration surface;
      a guidance support member comprising a first end and a second end, an attachment mechanism at the first end of the guidance support member for adjustable connection thereof at the attachment site of the reference frame, and an arcshaped constrained pathway extending between the first end and the second end of the guidance support member;

a shuttle comprising a first connection element and a second connection element, the first connection element configured for positionably attaching the shuttle to the guidance support member so as to contain movement of the shuttle along the constrained pathway, and the second connection element configured to provide a rotational coupler within the shuttle; and a cutting device comprising a proximal end and a distal end, a cutting portion configured at the distal end of the cutting device, and an attachment portion provided at the proximal end, wherein the cutting device is attached to the rotational coupler only within the shuttle at the attachment portion, with the distal end of the cutting device being free-standing relative to the reference frame, so as to allow rotational motion of the cutting portion as the shuttle is moved along the arc-shaped constrained pathway, thereby creating a shaped cavity from the initial cavity in the bone;

positioning the reference frame into the initial cavity; and moving the shuttle within the constrained pathway with the cutting device rotating so as to create the shaped cavity.

15. A bone milling instrument for creating a shaped cavity from an initial cavity in a bone, the bone milling instrument comprising:

a reference frame having a proximal end and a distal end, the reference frame defining a longitudinal axis between the proximal end and the distal end, a cylindrical member provided at the distal end of the reference frame, the cylindrical member configured for placement within the initial cavity so as to selectively maintain a relative positioning of the longitudinal axis of the reference frame and the bone with one another, a registration surface for engaging a portion of the initial cavity so as to establish a desired vertical position of the reference frame along the longitudinal axis, the registration surface located proximally of the cylindrical member, and an attachment site provided proximally of the registration surface;

a guidance support member having a first end and a second end, an attachment mechanism at the first end of the guidance support member for adjustable connection thereof at the attachment site of the reference frame and a constrained pathway extending between the first end and the second end of the guidance support member;

a shuttle having a first connection element and a second connection element, the first connection element configured for positionably attaching the shuttle to the guidance support member so as to allow movement of the shuttle within the constrained pathway, and the second connection element connected to a rotational coupler within the shuttle; and a cutting device having a proximal end and a distal end, a cutting portion configured at the distal end of the cutting device, and an attachment portion provided at the proximal end, wherein the cutting device is selectively attached to the rotational coupler within the shuttle so as to allow rotational motion of the cutting portion as the shuttle is selectively positioned within the constrained pathway so as to create the shaped cavity from the initial cavity in the bone wherein the reference frame is rotationally positionable about the longitudinal axis thereof so as to establish the orientation of the shaped cavity in the bone.

* * * * *